United States Patent [19]

Krauser

[11] Patent Number: 4,523,589
[45] Date of Patent: Jun. 18, 1985

[54] METHOD AND APPARATUS FOR TREATING AILMENTS

[76] Inventor: Robert S. Krauser, 444 Taconic Rd., Greenwich, Conn. 06830

[21] Appl. No.: 564,306

[22] Filed: Dec. 22, 1983

Related U.S. Application Data

[63] Continuation-in-part of Ser. No. 509,172, Jun. 29, 1983, abandoned.

[51] Int. Cl.³ .............................................. A61M 16/00
[52] U.S. Cl. ........................... 128/203.27; 128/204.17
[58] Field of Search ...................... 128/204.17, 203.26, 128/203.27, 207.28, 200.14, 200.23, 203.17, 399, 400; 604/23, 24, 26, 49, 54, 55, 291

[56] References Cited

U.S. PATENT DOCUMENTS

| | | | |
|---|---|---|---|
| 3,506,003 | 4/1970 | Gregory | 128/203.27 |
| 3,949,743 | 4/1976 | Shanbrom | 128/203.17 |
| 4,369,777 | 1/1983 | Lwoff et al. | 128/204.17 |
| 4,398,535 | 8/1983 | Guibert | 128/399 |
| 4,401,114 | 8/1983 | Lwoff et al. | 128/204.17 |

Primary Examiner—Henry J. Recla
Attorney, Agent, or Firm—Curtis, Morris & Safford

[57] ABSTRACT

A method and apparatus for the delivery of a vaporized pharmaceutical or medicant for the treatment and alleviation of ailments such as, cold symptoms, asthma and/or certain skin infections. A stream of air is heated and directed to the desired area and the medicant or pharmaceutical is vaporized into the air stream for delivery to the desired area. Preferably delivery is to the mucous or other membranes where it is absorbed by the body. In the treatment of colds the air is introduced into the nasal passages of the cold sufferer at a hyperthermia level. A vaporized microbicidal agent is introduced into the stream of air and into the nasal passages. The apparatus includes a housing containing a fan or blower and temperature control heating elements to warm the air. The housing includes a distribution area having nasal outlets for positioning on or about the nasal area of the user so that the warmed air is directed to flow into the nasal passages. A supply of microbicidal agent within the apparatus housing is introduced into the flow stream of the heated air by a spray device so that minute droplets of the microbicidal agent are entrained within the flow stream of the heated air. The combined effect of the heated air at hyperthermia levels and the microbicidal agent act on the cold viruses or bacterias housed in the nasal passages so as to alleviate cold systems.

9 Claims, 3 Drawing Figures

METHOD AND APPARATUS FOR TREATING AILMENTS

BACKGROUND OF THE INVENTION

This is a continuation-in-part of application Ser. No. 509,172, filed June 29, 1983 and now abandoned.

The present invention relates to a method and apparatus for treating a number of ailments for example, colds, asthma and certain other infections.

The common cold has persisted as an ailment affecting the human species since the earliest days of man. While great advances have been made over the years in dealing with numerous diseases, the common cold has endured as a persistent ailment which has heretofore defied effective treatment.

Recently it has been found that the common cold is caused by a virus. Additional research has uncovered the fact that a cold can be caused by in excess of one hundred different viruses and occasionally by bacteria. Thus the reason for the elusiveness of an effective cold remedy becomes apparent.

Cold viruses seem to find the temperature within the nose, about 33° C. or 91.4° F., more agreeable than the warmer climate of the blood and internal organs. The viruses attack the cells of the mucous membrane, producing congestion, sneezing and nasal drip. Some viruses have other effects, including aches, fever, coughing and chill. Colds take two to three days to incubate and last a week or so to run their course, declining slowly from an early peak. Sufferers are most infectious at the beginning, when sneezing and dripping are at their height. The virus kills the nasal cells it infects, and it takes time to regenerate them. That is one explanation of why it may take a while to recover from a cold.

For most adults, a cold is merely a nuisance. Sometimes it requires a day or two of bed rest, but more often it affects the victim with severe discomfort exemplified by a tired achey feeling. Children, however, often run a fever—and one adult cold virus, known as respiratory syncytial virus, can cause severe illness and even death in infants. Colds can also threaten adults suffering from chronic asthma and bronchitis.

The economic effect of colds is not negligible. The National Center for Health Statistics estimates that Americans caught 93 million colds—a rate of about 41.4 per 100—in 1981. But this total includes only cases that led to a visit to a doctor or restricted activity, 105 million days of bed disability and 32 million days off work. In 1979 (the most recent year for which figures are available), there were 11 deaths in which acute nasopharyngitis was listed as the sole cause of death.

Most viruses give immunity afterward, but only to that one virus. That is why small children seem to go from one cold to another, year round since their immunities are not in place. Adults tend to catch fewer colds year by year as acquired immunities build up.

Infuriating as it seems, after the decades of research into the complex of conditions called the common cold, there are still no useful suggestions for the ordinary sufferer. Once the cold has set in, the only treatment is to relieve symptoms.

Like all viruses, the ones that cause colds consist of a bit of genetic material, RNA or DNA, the two acids that constitute the genetic code, wrapped in a coat of protein. When the virus attacks the cell, the genetic chemicals enter the cell, then shed the coat. There they feed on the cell's genetic core, diverting it from its real function in the body and ordering it to build more viruses, which then leave the cell and repeat the cycle.

A cure for a cold presumably would have to invade the cell as well, destroying the virus without harming the cell.

Because it has been found that the cold virus exists predominately in the nasal passages where the temperature is lower, at 91.4° F., than other body areas, it has been reasoned that by artificially heating the nasal passages above 98.6° F., the cold virus might be killed or seriously weakened. The present invention applies earlier research into the uses of hyperthermia for various other human ailments to the problems of cold virus. Hyperthermia as it is used in this disclosure, and generally, has come to mean temperatures in humans above 41° C. or 106° F. induced with therapeutic intent.

Hyperthermia has shown various therapeutic advantages for a variety of ailments. More recently physical hyperthermia has been introduced to treat malignant cells in cancer therapy. Of significance, it is now assumed that some cancers are caused by viruses and changes in the genetic structure of the affected cells. In addition, it has been found that hyperthermia often shows synergism with X-irradiation and chemotherapy making combination therapy attractive. It has also been established that in general, malignant cells are more sensitive than normal cells in the range of 41° C. to 44° C., or 106° F. to 111° F. Medical researchers around the world report that heating malignant tissue to the hyperthermic range appears to be a safe and efficient means for either destroying the cancer cells or making them more susceptible to other forms of treatment. It has also been found by cancer researchers that immunal responses are stimulated by the application of controlled heat to the malignant areas. Controlled heat also increases the circulation of blood to the affected area, aiding in the carrying away of dead cell material as well as the rebuilding of new cells.

In developing the present invention, original experiments utilized only the application of heat of approximately 100° F. to 105° F. to the nasal passages. These experiments showed that cold symptoms, while not lasting the full seven to ten day cycle, were only reduced to a four to five day cycle. Greater effectiveness at this heat range may have been demonstrated by much longer exposure to the heat source, but convenience and tolerance especially among children were significant limiting factors. Experiments then continued with higher heat levels, 110° F. to 130° F., which produced better results than the lower levels but cold symptoms still lingered. The experiments continued with various temperature levels in combination with various microbicidal agents including hexylresorcinol and povidone-iodine. It was found that higher temperatures, which heated the nasal passages to approximately 106° F. to 113° F., in combination with the microbicidal agents hexylresorcinol and/or povidone-iodine resulted in cold symptoms disappearing within twelve to thirty-six hours.

It is believed that the combination treatment works best because the heated air seriously weakens the cold viruses and the concurrent or immediate introduction of the microbicidal agents further attacks the now weakened viruses, or occasionally bacteria, leading to their effective neutralization. The weakening or killing of the virus also acts as a catalyst to the body's immune system. The heat also increases the blood to the nasal passages, aiding in carrying away the dead cells and regenerating the new healthy cells in the nasal passages. Thus it was found that the treatment of early cold symptoms with heat and either hexylresorcinol or povidone-iodine, or both, usually resulted in their complete prevention or elimination within hours at most.

For fully developed colds, a combination of heat plus the microbicidal antiviral agents hexylresorcinol and/or povidone-iodine proved most effective, with elimination of symptoms within twelve to thirty-six hours. As used herein the term microbicidal agent means a germicide or antiseptic which, when applied in the nasal passages and used in conjunction with the application of heat to the nasal passages, produces an alleviation of cold symptoms in a cold sufferer. It is believed that the combination of the application of the microbicidal agent with hyperthermia treatment produces a significantly greater antiviral action.

The preferred choice of microbicidal agents, povidone-iodine and hexylresorcinol, was dictated by their demonstrated effectiveness in combination with the hyperthermia treatments. In addition both povidone-iodine and hexylresorcinol have proven to be effective while being non-toxic and non-irritating to the body or mucous membranes, after more than twenty-five years of use by the general public.

The leading povidone-iodine agent is sold under the trademark "Betadine" and this was the formulation used in the development of this invention. Povidone-iodine is a highly effective, broad spectrum topical microbicide for antiseptic use on skin, wounds and mucosa. It is employed widely in the hospital, clinic, office and home. Povidone-iodine differs physically and chemically from all other topical antiseptics and idophors and is recognized as the only non-detergent idophor presenting properties different from those of other germicidal iodine compounds or solubilized iodine mixtures. Povidone-iodine provides the following advantages: microbicidal activity, not merely bacteriostatic; broad spectrum microbicidal activity to kill both gram-positive and gram-negative bacteria (including antibiotic-resistant strains), tubercle bacillus, fungi, viruses, protozoa and yeasts; fast acting killing of most pathogens (except spores) within one minute in vitro with many organisms killed in only 15 to 30 seconds; microbicidal activity is maintained in the presence of blood, pus, serum and mucosal secretions; and virtually nonirritating and nonstinging to skin and mucus.

Hexylresorcinol was chosen due to its broad spectrum microbicide properties, low toxicity and soothing qualities. Development of the present invention has indicated effectiveness against the cold virus when used in combination with hyperthermia in preventing colds and in treating and eliminating existing cold symptoms.

In studies at Johns Hopkins Hospital published in the Bulletin of Johns Hopkins Hospital 41:21, 1927, Hexylresorcinol in a 1:1000 concentration in a glycerine-acqueous solution was shown to be completely effective against the common pathogenic bacteria including:

| Test Organisms | Control | 15 Seconds |
| --- | --- | --- |
| ESCHERICHIA COLI | + | 0 |
| EBERTHELLA TYPHOSA | + | 0 |
| PSEUDOMONAS PYOCYANEUS | + | 0 |
| PROTEUS VULGARIS | + | 0 |
| STAPHYLOCOCCUS ALBUS | + | 0 |
| STAPHYLOCOCCUS AUREUS | + | 0 |
| CORYNEBACTERIUM DIPHTHERIAE | + | 0 |
| CORYNEBACTERIUM HOFMANNI | + | 0 |
| STREPTOCOCCUS HAEMOLYTICUS | + | 0 |
| STREPTOCOCCUS VIRIDANS | + | 0 |
| PNEUMOCOCCUS TYPE I | + | 0 |
| PNEUMOCOCCUS TYPE IV | + | 0 |
| NEISSERIA MENINGITIDIS | + | 0 |
| NEISSERIA GONORRHOEAE | + | 0 |
| VIBRIO METCHNIKOVII | + | 0 |

+ = Growth
0 = Sterile

Over the years hexylresorcinol has shown to have antimicrobicidal effects and has also been used as a gargle and a urinary antiseptic. It has been shown to be effective as a urinary antiseptic in killing microbes in the urine in concentrations ranging from 1:60,000 to 1:18,000. Other germicidal studies have shown effectiveness in dilutions as high as 1:5000. In the development of the present invention hexylresorcinol in dilutions of 1:2000 in a glycerine-acqueous solution were used and occasionally dilutions of 1:1000 were also used.

Other applications for hexylresorcinol over the years have included application for cuts, abrasions, burns, sunburns, athletes foot and the hygienic care of the mouth as a mouthwash, gargle and application after tooth extraction. Hexylresorcinol is also used as the active ingredient in a leading throat lozenge.

According to the Federal Register, Volume 47, no. 101, May 25, 1982, a panel commissioned by the Federal Drug Administration found hexylresorcinol in concentrations at least as high as 1:1000 to be safe for topical applications to the mucous membranes of the mouth and throat.

Various prior art devices have been proposed for the treatment of respiratory or infectious problems. The Stuart device, U.S. Pat. No. 1,239,634, produces a flow of warmed air to the patient but not at hyperthermia levels. However, the Stuart device will not be effective against colds as the amount of heat produced is virtually unregulated and not sufficiently high enough. This differs substantially from the invention disclosed herein which produces controlled heated air to take advantage of the properties of hyperthermia. The Stuart device, using the disclosed filter, produces a very unmeasured amount of medicant as there is no way of controlling how much medicant is released from the medicated cotton over a given period of time.

The Mascolo device, U.S. Pat. No. 1,965,424, utilizes steam passing through a closed cup of medicant. Again this device fails to present a means of controlling the temperature of the steam which is probably dangerously high, especially for children. The towel disclosed therein purportedly protects the face from the boiling steam, but again it is difficult to ascertain the amount of thermal protection and the amount of medicant being delivered to the face and to the nasal passages, if any.

The Inoue device, U.S. Pat. No. 2,047,324, provides for the delivery of volatile matters or medicinal matters fumigated by means of an electric heating device and a forced draft. Again the device provides no control as to the amount of heat or the amount of medicant provided to the user.

The Conlin device, U.S. Pat. No. 3,522,236, provides a means of delivering vapors, perhaps medicated, to the user with a crude means of temperature control. Again the amount of medicant and the temperature range of the vapors are difficult to carefully regulate.

Specifically, such previous apparatus do not incorporate controlled conditions of temperature or medicant delivery which is important to the efficacy of an effective cold treatment procedure and especially in the safe treatment of the patient, and none disclose a way of stopping the medicant without shutting down the entire device.

Additionally, such previous apparatus have not specifically recognized the advantages of combining hyperthermia with any specific microbicides for the treatment of the common cold. More specifically none disclose or teach the advantages of either hexylresorcinol or povidone-iodine in their treatment, nor do they appear to provide an especially convenient means of treatment in terms of comfort or time with these obvious advantages. These noted prior art devices are also bulky, barely portable and certainly not lightweight and handheld as is the device of the present invention with its obvious advantages particularly in treating another patient.

It is therefore an object of the present invention to provide a method and apparatus to provide an effective treatment to alleviate the symptoms of the common cold in a cold sufferer.

It is a further object of the present invention to provide a simple yet effective method and apparatus to treat symptoms of the common cold through the use of hyperthermia by warming the nasal passages of the cold sufferer and then providing for the application of a microbicidal agent within the nasal passages.

A still further object of the present invention is to provide an apparatus for the treatment of the common cold which effectively combines the ability to heat the nasal passages of a cold sufferer to hyperthermic levels and to selectively deliver a microbicidal agent in convenient dosage to the warmed nasal passages.

Yet another object of the present invention is to provide such apparatus in a simple to construct, lightweight form which is conveniently handheld so as to be relatively simple and easy to use.

A still further object of the present invention is to provide such apparatus wherein a selected microbicidal agent may be dispensed in a controlled quantity so as to effectively provide a convenient dosage of the selected medicant.

Yet another object of the present invention is to provide an apparatus to deliver a variety of medicants for topical or internal use especially in instances where the mucous membranes may effectively and expeditiously absorb the prescribed medicant.

SUMMARY OF THE INVENTION

The present invention resides in a method and apparatus for preventing a cold or treating a cold in a cold sufferer wherein an air stream is heated to 110° to 130° F. The air stream is introduced into the nasal passage of the cold sufferer for a selected period of time and subsequently, an effective amount of sprays containing droplets of microbicidal and anti-viral agents, to apply a coating to the nasal passage lining, is also injected into the nasal passage in a timed concurrent or sequential relationship to the introduction of the heated air.

The apparatus successfully provides for the delivery of heat and the chosen microbicidal agents to combine in a synergistic manner to kill or seriously weaken the cold virus and/or bacteria. A device for carrying out the above method comprises a housing having air entry and air exit ports wherein air is drafted into the housing via the entry port by a fan which along with its drive are contained in the housing. The fan draws air across a heating element to produce a stream of heated air having a temperature in the range of 110° F. to 130° F. The housing is supplied with temperature control means to maintain proper temperature including a rheostat for preselecting current and hence heat range as well as a thermostat inserted in the cylinder in advance of the distribution area, which will shut off current to the heating element at a preselected maximum heat range. The continued action of the fan bringing in cool air will rapidly cool down the heating elements. The apparatus with the heating element turned on again at a predetermined minimum temperature, as controlled by the thermostat, maintains a regulated warm air flow to insure maintenance of a hyperthermic flow of air.

The heated air is then forced from the housing through the exit port into the distribution area with the distribution area being adapted to distribute the heated air into the nasal passages of the cold sufferer.

The distribution area has nasal outlets directing the heated air and/or spray to the nasal passages. A fine spray of medicated droplets is selectively released to apply a medicated coating to the mucous lining of the nasal passages. The spray, having its own means of propulsion, may also be sprayed into the nasal passages independent of the forced heated air. Alternate means of providing the spray might be an attached atomizer bulb with a tube entering the housing or an electric piston pump instead of the mechanical pump. Alternatively, the air may be forced over a porous absorption material impregnated with the microbicidal agent.

In another embodiment of the present invention other prescribed medicants may be introduced through the mucous membranes for the treatment of other ailments or topically applied to other areas of the body.

DESCRIPTION OF THE PREFERRED EMBODIMENT

Figure 1:
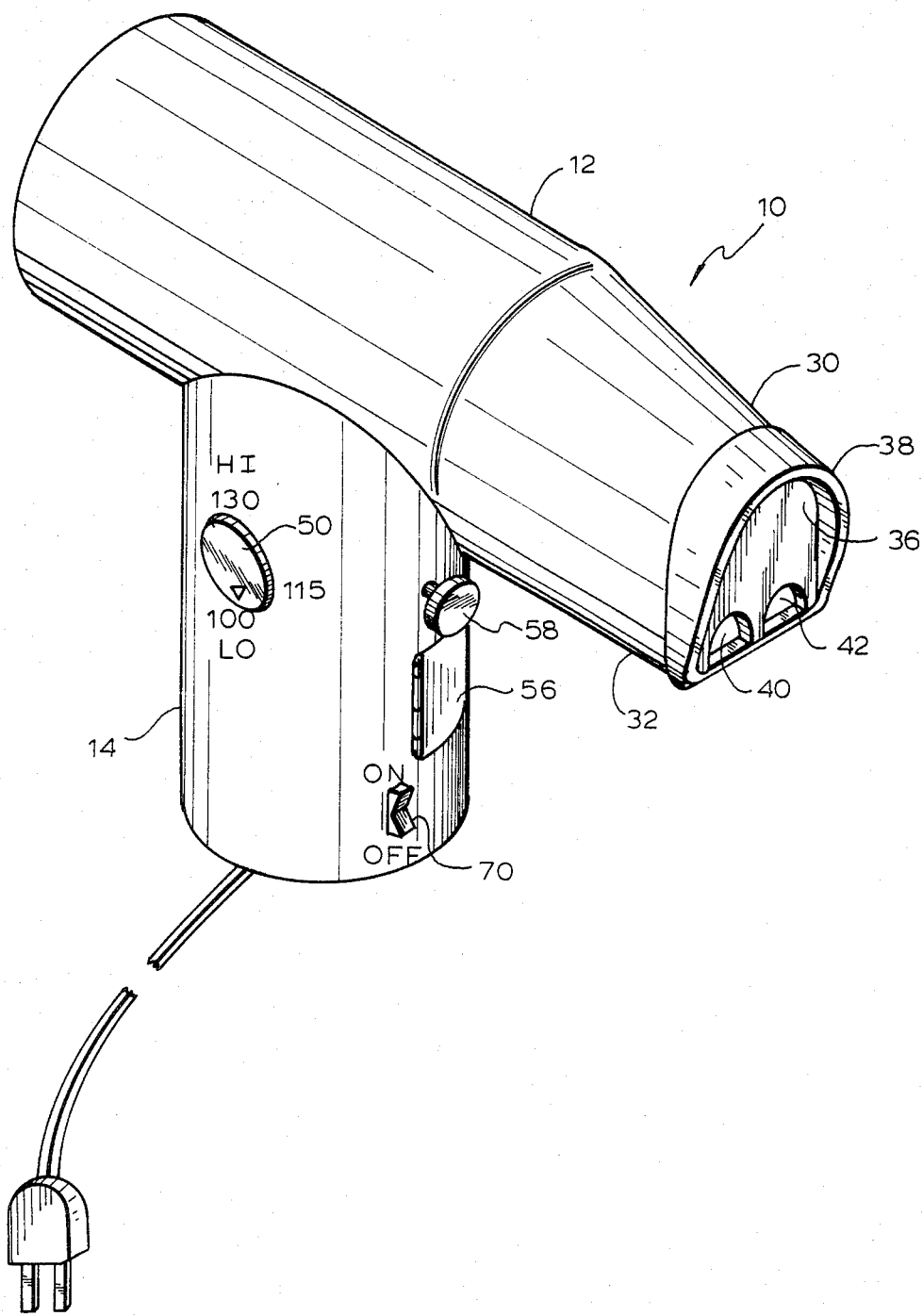
FIG. 1 is a perspective view of the apparatus of the present invention.

With reference to the drawing, the apparatus 10 for the treatment and alleviation of cold symptoms comprises a housing 12 having a handle portion 14 defining interior chambers 16 and 18, respectively. One end 20 of the chamber 16 is open to the atmosphere to provide an air intake opening and the other end 22 of the chamber 16 is also open to define an air outlet pasage. A filter screen 24 is preferably fitted within opening 20 to filter out dust particles. Preferably housings 12 and 14 are formed of lightweight high strength molded plastic material so the device is readily adapted for ready portability and ease of use.

Mounted within chamber 16 in housing 12 is a fan or blower 26 positioned and oriented to draw atmospheric air through opening 20 and screen 24 into chamber 16. The air flow passes through a heating device 28 and continues under the action of blower 26 after being warmed by the heater 28 to exit opening 22.

Figure 2:
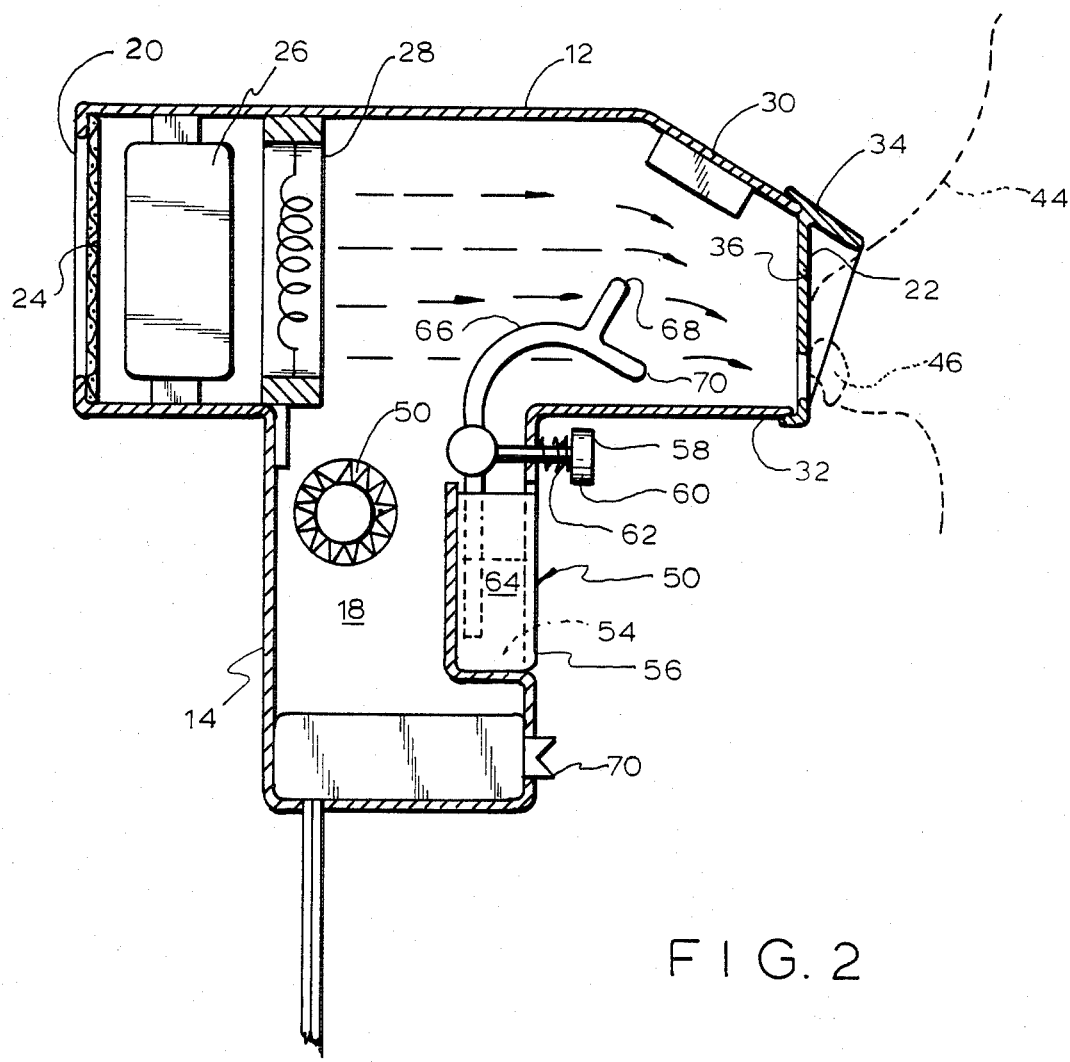
FIG. 2 is a vertical cross-section diagramatically illustrating the device of the present invention.
Figure 3:
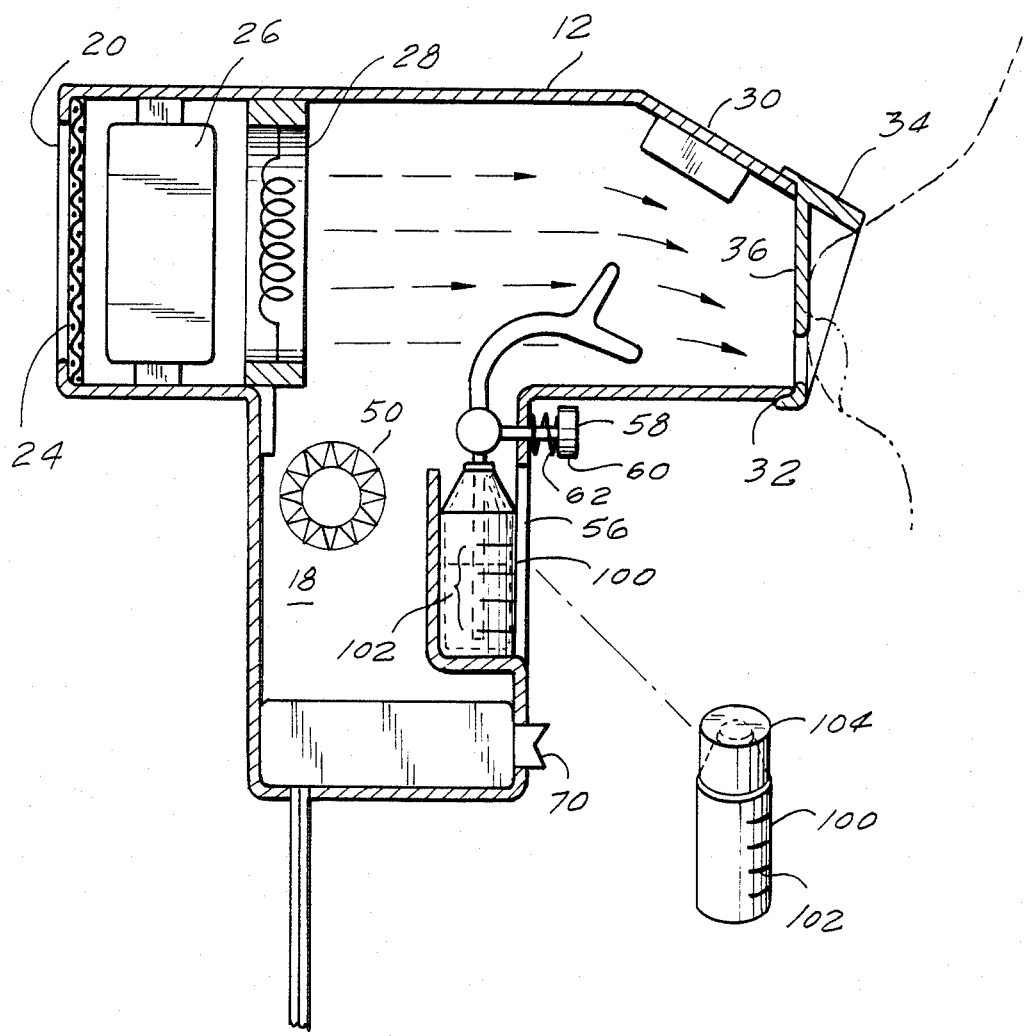
FIG. 3 is a diagrammatic representation of a capsule containing premeasured quantities of a desired medicant which may be used in another embodiment of the invention.

Housing 12 and chamber 16 are configured so that the upper wall segment 30 adjacent opening 22 converges towards the lower wall segment 32 to direct the flow of air flowing through chamber 16 toward the lower wall segment 32. An end pad 34 adapted to snap fit over opening 22 is provided. End pad 34 includes a wall segment 36 which covers opening 22 and an extending shroud like member 38 which recedes from an extending position at its upper extremity to its lower extremity which is in juxtaposition with the wall 36. A pair of access ports 40 and 42 are provided in the lower portion of wall 36 and the access ports 40 and 42 are designed to direct the flow of air from the apparatus 10 to the nostril of a user of the device. To this end the snap on end pad 34 is preferably made of a somewhat pliable rubber-like material for comfort and convenience in use. As illustrated in FIG. 2, the nose 44 of an intended user of the device may be pressed against end wall 36. This action tends to elevate the position of the nostrils, indicated at 46 to locate the nostrils of a user of the device in convenient position over the air exits ports 40 and 42.

A control thermostat 48 is also provided at a convenient location within housing 16 to measure the temperature of the air flowing therethrough.

The temperature of the air warmed by heater 28 may be conveniently controlled by a variable device such as a rheostat 50. Adjustment of rheostat 50 varies the current flowing to the heater element 28 thereby controlling the heat output of heater 28 to control the heat input to the air flowing over the heater. The air is maintained at the desired heat level, as indicated by the adjustment of rheostat 50, as the thermostat 48 periodically turns heater 28 on and off to maintain air temperature at the desired setting.

Mounted within housing 14 in chamber 18 is a medicant dispersant assembly 52 which includes a reservoir 54 fillable through an access panel 56 with the desired microbicidal agent or agents. A plunger operated pumping system 58 comprising a depressable plunger member 60 acting against a coil spring 62 acts to dispel the microbicidal agent 64 within reservoir 54 through a delivery tube 66 to outlet orifices 68 and 70 positioned within the flow stream of air flowing under the action of blower 26 within chamber 16. The outlet orifice 68 and 70 are conveniently positioned to deliver minute droplets of liquid spray into an area of chamber 16 adjacent the outlet ports 40 and 42 for convenient inhalation by a user of the device. The air flowing under action of blower 26 entrains the minute droplets of the microbicidal agent to assist in the inhalation of the desired medicant.

The spray device 58 may also be operated independently of blower actuation thus affording use of the device as an inhalation device without the flow of warmed heated air. The device may also be operated with the blower and spray alone without activating the heater element 28 to assist in the dispersion of the minute droplets of medicated spray, if desired.

Blower 26 is activated by a conveniently placed on/off switch 70 and it is also recognized that while an A.C. electrical power cord connection 72 is illustrated it is contemplated that battery operated motor and heating element may also be utilized, such battery being the type which may be conveniently recharged by a recharger assembly which may be inserted into any standard electrical outlet.

Because the heating element to elevate the temperature of the flowing air need not be of overly large capacity and the blower need only direct a relatively modest flow of air, the device is advantageously of a relatively compact and lightweight construction facilitating convenient handheld use.

In another embodiment of the present invention the medicant is supplied in a clear plastic capsule 100 which preferably includes suitable indicia 102 thereon in the form of scribed or marked lines which represent a prescribed dosage for application. Capsule 100 includes a removable top 104 or a suitable tear off top and is adapted to sealingly fit about the pump tube of pump system 58. Preferably, access port 56 is of a clear plastic material to enable the user to visually discern the medicant within capsule 100 so that the proper dosage for the spray may be determined by viewing the indicia on capsule 100. Use of capsule 100 may be preferable for ease of use and replacement of medicant. Capsule 100 may be made disposable for ease in use and may be pre-filled with the desired medicant.

In a preferred embodiment of the present invention the microbicidal agent hexylresorcinol was used. Hexyresorcinol, an aromatic alcohol, is dihydrobenzene with a normal hexyl group on position 4 and hydroxyl groups on positions 1 and 3 of the aromatic nucleus. Typically hexylresorcinol is prepared by condensing rescorcinol with caproic acid in the presence of zinc chloride and the resulting intermediate product is reduced to hexylresorcinol. In a preferred embodiment a 0.05 to 0.1 percent concentration of hexylresorcinol was used as the microbicidal agent in the apparatus of the present invention. Heat was applied to warm the air to between 110° F. to 130° F. to induce an elevated temperature within the nasal passages of the user to a hyperthermia level, i.e. above about 106° F. The heated air was supplied at intermittent periods for comfort and periodically spray mists of the hexylresorcinol in sufficient amounts to effectively coat the nasal passages were induced to enter the warmed nasal passages.

One recommended procedure is the introduction of the microbicidal spray into the nasal passage in a timed relationship to the introduction of the heated air stream and forms a sequence of operation which can be repeated to form a treatment cycle such that the heated air may be introduced for a number of intervals each heat interval being of less than 15 seconds, with five second rest intervals between. The heat interval and the rest period are repeated four or five times, and in the last two intervals the microbicidal spray is introduced.

The procedures can best be described from the following flow chart:

| Step 1 | 1a | Step 2 | 2a | Step 3 | 3a | Step 4 | 4a | Step 5 | 5a |
| --- | --- | --- | --- | --- | --- | --- | --- | --- | --- |
| Heat 15 sec | rest 5 sec | Heat 15 sec | rest 5 sec | Heat 15 sec | rest 5 sec | Heat 15 sec spray 3 sprays | rest 5 sec | Heat 15 sec spray 3 sprays | rest and 3 sprays |

The treatment cycle is repeated three to four times per day, spaced equally apart if possible. This is a recommended sequence although it is to be understood that depending upon the tolerance level of the individual, larger periods of application of heated air may be employed, if desired, and more spray may be utilized to result in greater inhalation of the microbicidal agent. The procedure described above was found to be effective to relieve cold symptoms in a number of individuals and to significantly speed their recovery from the undesirable effects of a cold.

In another preferred embodiment povidone-iodine was used in a similar application technique as that described above. Povidone-iodine is also known as 1-ethenyl-2-pyrrolidinone polymers; 1-vinyl-2-pyrrolidinone polymers; poly [1-(2-oxo-1-pyrrolidinyl)] ethylene; polyvinylpyrrolidone; polyvidone; polyvinylpyrrolidone and polvidone. Povidone-iodine is made synthetically by interacting 1,4 butanediol with ammonia and acetylene. The preferred concentration of povidone-iodine used in practice of the present invention was a 7.5 percent concentration diluted 1:14 or a 0.5 percent concentration.

In yet another preferred embodiment of the present invention, equal parts of the disclosed hexylresorcinol and povidone-iodine were mixed to make a combination microbicidal agent and, also, alternate treatments of hexylresorcinol and povidone-iodine were employed.

The invention disclosed herein is not limited to use of hexylresorcinol and povidone-iodine, either singly, in combination or in alternate treatment applications. A number of antiseptics and antiviral agents are believed to be useful as microbicidal agents in the practice of the present invention. The following compositions used either singly, in combination or in alternate treatment applications are believed to offer significant benefits to a cold sufferer when applied in a hyperthermic treatment made as disclosed herein. This listing is not intended to be exhaustive but merely illustrative of the types of microbicidal agents which may be effectively employed as a treatment agent in conjunction with the method and apparatus disclosed herein:

Benzyl alcohol also known as phenyl methanol in 0.05 to 10.0 percent concentration solution.

Menthol also known as hexadyhdrothymol or 3-paramenthol in a 0.04 to 2.0 percent concentration solution.

Phenol or hydroxybenzene in a 0.5 to 1.5 percent concentration.

Phenolate sodium also known as sodium phenolate, sodium phenate, sodium carbolate, sodium phenoxide and phenol sodium in a 0.5 to 1.5 percent concentration solution.

Salicyl alcohol having chemical structure ortho-hydroxy benzyl alcohol in a 1.0 to 6.0 percent concentration solution.

Eucalyptol which is a volatile oil prepared by steam distallation of the fresh leaves of eucalyptus globulus in a 0.025 to 0.1 percent concentration solution.

Methyl salicylate the methyl ester of salicylic acid made by esterfying methyl alcohol with salicylic acid in up to a 0.4 percent concentration solution.

Thymol also known as thyme camphor is a 5-methyl-2-isopropyl-1-phenol in a 0.006 to 0.1 percent concentration solution.

Cresol, a phenol with a methyl group on either the ortho, meta, or para positions of the benzene ring, also known as tricresol, methylphenol or cresylic acid in a 0.25 to 0.5 percent concentration solution.

Sodium dichromate, the sodium salt of chromic acid having the empiric formula $Na_2CrO_4.4H_2O$ in 2.0 to 3.0 percent concentration solution.

Benzalkonium chloride, a mixture of alkyldimethylbenzylammonium chlorides with the empiric formula $[C_6H_5CH_2N(CH_3)_2R]$ where R represents alkyl groups of varying lengths beginning with n-$C_8H_{17}$ to n-$C_{18}H_{37}$, in a 0.01 to 0.02 percent concentration solution.

Benzethomium chloride which is benzyldimethyl [2-[2-(p-1,1,3,3-tetramethylbutylphenoxy) ethyoxyl-]ethyl] ammonium chloride in a 0.02 to 0.1 percent concentration solution.

Benzoic acid also known as phenylcarboxylic acid, phenylformic acid, flowers of benzoin and flowers of benzamine, in a 0.1 to 0.3 percent concentration solution.

Carbamide peroxide in anhydrous glycerin also known as urea hydrogen peroxide having the empiric formula $CO(NH_2)_2.H_2O$ in a 9.0 to 15.0 percent concentration solution in anhydrous glycerin or propylene glycol.

Cetylpyridinium chloride or 1-hexadecylpyridinium chloride in a 0.025 to 0.1 percent concentration solution.

Dequalinium chloride in a 0.5 percent concentration solution.

Domiphen bromide or N,N-dimethyl-N-(2-phenoxyethyl-1-dodecyldimethyl (2-phenoxyethyl) ammonium bromide in a 0.005 percent concentration solution.

Ethyl alcohol, $C_2H_5OH$, also known as hydroxyethane, ethanol and ethyl hydroxide, in up to 70 percent concentration solution.

Iodine in 1.0 to 2.0 percent concentration solution.

Oxyquinoline sulfate also known as oxine, 8-hydroxyquinoline, oxybenzopyridine, phenopyriden, 8 quinolinol and oxychinolin in up to a 0.1 percent concentration solution.

Secondary amyltricresols prepared by the interaction of ortho-, meta and paracresols and secondary amyl alcohol at 150° C. in 0.1 to 0.3 percent concentration solution.

Sodium caprylate, which is the sodium salt of caprylic acid ($CH_3(CH_2)_6COONa$) and is an aliphatic, straightchained carboxylic acid in a 10.0 to 20.0 percent concentration solution.

Thymoliodide also known as dithymol diiodide in a 2.0 to 10.0 percent concentration solution.

Citric acid, 2-hydroxy-1,2,3-propanetricarboxylic acid, in an aqueous solution of between 0.5% to 5%.

As indicated this listing is by no means exhaustive but is merely indicative of the general class of microbicidal agents which will be effective for use in the present invention. The concentrations noted are also not intended to be limiting but are suggested based on recommendations of safety in data supplied by the Food and Drug Administration. It is also to be noted that all of the recommended microbicidal agents may be used singly or in combination or in alternate applications, if desired, to act on a wide range of viri and bacteria.

In addition it has been found that the apparatus of the present invention may be used as a delivery vehicle for a wide variety of medicants for topical or internal use. In terms of internal use it is widely recognized that the mucous membranes are an optimal site or entry point for the absorption of drugs and/or medicants into the body. Medicants entering through the mucous membranes often act much faster and more effectively than pills or capsules ingested in the stomach, or even injections.

Medicants heated above body temperature for example, about 100° F., and entering through the mucous membranes may act faster and be absorbed more effectively than medicants which are not delivered at an elevated temperature.

In addition the device may be used for the application of medicants in a topical manner on other parts of the body. As an example of topical application it has been found that the topical application of the quartenery ammonium compound benzalkonium chloride is substantially more effective when heated to 37° C. for treatment of streptococcus haemolyticus, staphyloccus aureus, eberthella hyphosa and escherichia coli than when it is applied at 20° C.

Further, the device of the present invention has been found to be effective to heat and dry the area between the toes and legs prior to the application by spray of a medicant with anti-fungal agents.

It is thus seen that the present invention provides a new and novel method and apparatus to alleviate the symptoms of a cold by combining the use of the beneficial aspects of hyperthermic treatment through the use of dry heated air in combination with a microbicidal agent. In addition, the present invention provides a method and apparatus for delivery of other medicants for ultimate absorption through the mucous membrane or any other absorptive membranes and for topical applications of medicants and anti-fungal agents.

What is claimed is:

1. A method for alleviating symptoms of a viral and/or bacterial infection comprising the steps of:
   warming air to a temperature above 105° F. so it is relatively dry,
   directing a stream of the warmed and relatively dry air to the nasal passages of a person to be treated, and
   spraying a measured quantity of a misted microbicidal agent for inhalation into the nasal passages thereby to coat the membranes within the warmed nasal passages with said microbicidal agent.

2. The method as defined in claim 1 wherein said stream of warmed air is directed to the nasal passages intermittently.

3. The method as defined in claim 1 wherein said stream of warmed air is directed to the nasal passages intermittently and said microbicidal agent is sprayed during periods when said warmed air is not flowing.

4. The method as defined in claim 1 wherein said air is warmed to the desired temperature range responsive to a thermostatic control device.

5. The method as defined in claim 1 wherein said microbicidal agent is selected from the group consisting essentially of hexylresorcinol, povidone-iodine, citric acid, benzyl alcohol, menthol, phenol, phenolate sodium, salicyl alcohol, eucalyptol, methyl salicylate, thymol, cresol, sodium dichromate, benzalkonium chloride, benzethomium chloride, benzoic acid, carbamide peroxide, cetylpyridinium chloride, dequalinium chloride, domiphen bromide, ethyl alcohol, iodine, oxyquinoline sulfate, secondary amyltricresols, sodium caprylate and thymoliodide.

6. The method as defined in claim 1 wherein said microbicidal agent is hexylresorcinol in a 0.05 to 0.1 percent concentration solution.

7. The method as defined in claim 1 wherein said microbicidal agent is povidone-iodine in a 0.5 percent concentration solution.

8. The method as defined in claims 5, 6, or 7 wherein the procedure entails directing warmed air in a sequence of steps comprising flowing warmed air, resting, flowing warmed air and directing the said microbicidal agent during said period of rest.

9. The method as defined in claim 1 wherein said air is warmed to a temperature of between 105°F. to 130°F.

* * * * *